(12) United States Patent
Gelikonov et al.

(10) Patent No.: US 7,515,274 B2
(45) Date of Patent: Apr. 7, 2009

(54) METHOD FOR OBTAINING THE IMAGE OF AN OBJECT, DEVICE FOR CARRYING OUT SAID METHOD AND DEVICE FOR DELIVERING LOW COHERENT OPTICAL RADIATION

(75) Inventors: Grigory Valentinovich Gelikonov, Nizhny Novgorod (RU); Valentin Mikhailovich Gelikonov, Nizhny Novgorod (RU); Alexey Victorovich Myakov, Nizhny Novgorod (RU); Felix Isaakovich Feldchtein, Cleveland, OH (US)

(73) Assignee: Imalux Corporation, Cleveland, OH (US)

( * ) Notice: Subject to any disclaimer, the term of this patent is extended or adjusted under 35 U.S.C. 154(b) by 167 days.

(21) Appl. No.: 10/516,810

(22) PCT Filed: Jun. 4, 2003

(86) PCT No.: PCT/RU03/00252
§ 371 (c)(1),
(2), (4) Date: Jun. 20, 2005

(87) PCT Pub. No.: WO03/104845
PCT Pub. Date: Dec. 18, 2003

(65) Prior Publication Data
US 2006/0165350 A1    Jul. 27, 2006

(30) Foreign Application Priority Data
Jun. 7, 2002    (RU) ............................ 2002114935

(51) Int. Cl.
*G01B 9/02* (2006.01)

(52) U.S. Cl. .................. 356/479; 356/497; 250/227.19; 250/227.27

(58) Field of Classification Search ............... 356/479, 356/497; 250/227.19, 227.27
See application file for complete search history.

(56) References Cited

U.S. PATENT DOCUMENTS 5,321,501 A    6/1994    Swanson et al.

(Continued)

FOREIGN PATENT DOCUMENTS

EP    1 077 360    2/2001

(Continued)

OTHER PUBLICATIONS

EP Communication for Application No. 03 757 222.9 dated Aug. 24, 2007.

*Primary Examiner*—Tarifur R. Chowdhury
*Assistant Examiner*—Jonathon D Cook
(74) *Attorney, Agent, or Firm*—Renner, Otto, Boisselle & Sklar, LLP

(57) ABSTRACT

The invention relates to studies of internal structures of objects with the aid of optical means. According to the invention an optical system (15) of the delivering device for low coherence optical radiation, in a particular embodiment, an optical fiber probe (8), includes at least two lens components (19), (20), which have a positive focal power and are positioned substantionally confocally. This ensures a constant propagation time for the low coherence optical radiation propagating from a given point of the transverse scanning surface (28) or (39) to a corresponding conjugate point of the image plane (22). That provides elimination of the transverse scanning related aberration of the optical path length for low coherence optical radiation directed towards the object (11) both for a flat transverse scanning surface (28) and for a transverse scanning surface (39) having a curvature. In another embodiment, together with the substantionally confocal arrangement of lens components (19), (20), the longitudinal scanning is performed by varying the optical path length for the low coherence optical radiation propagating from the transverse scanning surface (28) to the optical system (15), i.e., from the end face (17) of the distal part (18) of the optical fiber (14) to the optical system (15). To achieve this, a device for longitudinal scanning (10) is incorporated into the optical fiber probe (8). This ensures a corresponding shift of the focusing position of the low coherence optical radiation during longitudinal scanning, i.e., allows for alignment of the focusing position of the low coherence optical radiation with the position of the coherence gate and, consequently, their simultaneous movement.

35 Claims, 6 Drawing Sheets

U.S. PATENT DOCUMENTS

| | | |
|---|---|---|
| 5,737,112 A | 4/1998 | Iizuka |
| 6,069,689 A | 5/2000 | Zeng et al. |
| 6,124,930 A | 9/2000 | Fercher |
| 6,445,939 B1 * | 9/2002 | Swanson et al. ............ 600/342 |

FOREIGN PATENT DOCUMENTS

| | | |
|---|---|---|
| EP | 1 154 224 | 11/2001 |
| RU | 2 148 378 | 5/2000 |

* cited by examiner

METHOD FOR OBTAINING THE IMAGE OF AN OBJECT, DEVICE FOR CARRYING OUT SAID METHOD AND DEVICE FOR DELIVERING LOW COHERENT OPTICAL RADIATION

TECHNICAL FIELD

The present invention relates to physical engineering, in particular, to studies of internal structures of objects with the aid of optical means, and can be applied for obtaining an image of an object using low coherence optical radiation in medical diagnostics of individual organs and systems of human body in vivo or in vitro, as well as in industrial diagnostics such as control of technological processes.

BACKGROUND ART

Apparatus for imaging an object using low coherence optical radiation are fairly well known. Such apparatus comprise a low coherence light source optically coupled with an optical interferometer and a photodetector, which is connected with a data processing and displaying unit. The optical interferometer is typically designed either as a Michelson optical fiber interferometer or as a Mach-Zender optical fiber interferometer. Regardless of the specific design used, an optical interferometer typically comprises one or two beam splitters, a measuring arm and a reference arm. The measuring arm includes, as a rule a measuring probe, which is most often an optical fiber probe, and is designed to deliver low coherence optical radiation to the object, the reference arm having a reference mirror at its end. Longitudinal scanning of the object is performed either by connecting the reference mirror with an element that provides mechanical movement of the reference mirror, or by fixing the position of the reference mirror and performing longitudinal scanning with the aid of a piezoelectric scanning element.

A virtue of optical interferometers applied for studying objects with the use of low coherence optical radiation is a potential for acquisition of images of turbid media with high spatial resolution as well as noninvasive diagnostics in medical studies and non-destructive control in diagnostics of various equipment.

Prior improvements of apparatus for imaging an object using low coherence optical radiation are aimed, generally, at enhancing the resolution of the apparatus, as known, or ensuring efficient use of optical source power by providing optimal signal-to-noise ratio.

The measuring probe incorporated into the measuring arm performs the function of delivering low coherence optical radiation to the object. Known measuring probes are designed typically as an optical fiber probe comprising an optical fiber positioned in such a way, that low coherence optical radiation can pass from its proximal end to its distal end, and an optical system which focuses the low coherence optical radiation on the object. The optical system includes at least one lens component with positive focal power. The measuring probe includes also a system for transverse scanning of the low coherence optical radiation. The measuring probe typically has an elongated body with a throughhole extending therethrough, wherein an optical fiber extends. The transverse scanning system includes an actuator, which may be a piezoelectric element, stepper motor, electromagnetic system or electrostatic system.

Improvements of measuring probes known in the art, which are incorporated into apparatus for imaging an object using low coherence optical radiation are aimed at imaging thin vessels, and at optimizing the probe design for obtaining a maximum amplitude of optical beam deviation with limited size of the body of the optical fiber probe.

Prior apparatus for imaging an object using low coherence optical radiation execute intrinsically the same method for obtaining an image of an object. According to this method, the low coherence optical radiation is directed simultaneously towards the object and along the reference optical path. The optical radiation is directed therewith towards the object through an optical system, which focuses the low coherence optical radiation onto the object, the optical radiation being transversely scanned over a surface approximately orthogonal to the direction of propagation of the optical radiation. Then the optical radiation having returned from the object is combined with the optical radiation, which passed through the reference optical path. The optical radiation, which is a result of the combining, is used to visualize the intensity of the optical radiation having returned from the object. In addition, longitudinal scanning of the object is performed by varying the difference in optical path lengths for the low coherence optical radiation directed towards the object and directed along the reference optical path. The difference in the optical path lengths is varied by at least several tens of wavelengths of optical radiation in compliance with a predetermined rule.

Another apparatus executes the above imaging method and comprises a low coherence optical light source optically coupled with an interferometer and at least one photodetector, the output of the photodetector being connected with a data processing and displaying unit. The interferometer includes a beam splitter optically coupled with a measuring arm and a reference arm, the measuring arm being provided with a delivering device for low coherence optical radiation designed as an optical fiber probe.

The delivering device for low coherence optical radiation is designed as an optical fiber probe. The optical fiber probe comprises an optical fiber, which is positioned allowing for the low coherence optical radiation to pass from the proximal end of the optical fiber probe to its distal end, an optical system, and a system for transverse scanning of the low coherence optical radiation. The optical system is optically coupled with the optical fiber and is used for focusing the low coherence optical radiation onto the object. The optical system comprises at least a first lens component with positive focal power. The optical fiber is incorporated into the transverse scanning system, which is arranged capable of moving the end face of the distal part of the optical fiber over the transverse scanning surface in a direction approximately perpendicular to the own axis of the optical fiber.

A drawback of the prior method, as well as of the apparatus described above for executing this method, of delivering low coherence optical radiation towards the object, as well as of any other prior technique for imaging an object using low coherence optical radiation, is that the acquired image of a flat object looks bent. This occurs due to peculiarity of imaging with the use of an interference signal, which results from combining optical radiation coming back from the object with that of the reference path. It is known that the interference signal occurs when optical path lengths for the low coherence optical radiation directed towards the object, and of the reference path are equal. However, the propagation time for the low coherence optical radiation from points, having different off axis positions in a flat transverse scanning surface, to corresponding conjugate points in the image plane is not the same. Therefore, while the optical path length for the low coherence optical radiation propagating along the reference arm is constant, the optical path length for the low coherence optical radiation directed towards the object is not constant when transverse scanning is performed. That results in a curvature of the acquired images. The later can be seen in FIG. 19, showing an example of an image acquired by the prior method, and in FIGS. 8, 9 and 10 which demonstrate prior image construction.

FIG. 8 illustrates construction of an image by the known method in prior art apparatus for a flat transverse scanning surface 28 in a case when an optical system 29 is designed as a single lens component 30 with positive focal power. Line 31 seen in the drawing corresponds to a point locus, to which the optical path length for the low coherence optical radiation passing to the object 11, has the same value from corresponding conjugate points disposed at various off axis positions in a flat transverse scanning surface 28.

FIG. 9 and FIG. 10 illustrate image construction by the known method in prior apparatus for a flat transverse scanning surface 28 in cases when the optical system 29 is designed as two lens components 32, 33 with positive focal power, the lens components being placed from each other at a distance that is respectively, either greater or smaller than the confocal distance. FIG. 9 shows also a line 34 and FIG. 10 shows a line 35, that correspond each to a point locus, to which the optical path length for the low coherence optical radiation passing to the object 11, has the same value from corresponding conjugate points disposed at various off axis positions in a flat transverse scanning surface 28. It is evident from the drawings that lines 31, 34, 35 have a curvature. In addition, in the case when the transverse scanning surface has a curvature, for instance, when the optical fiber in the optical fiber probe serves as a flexible cantilever, there occurs an additional aberration that also contributes to the curvature of the image being constructed. Another disadvantage of prior technique, is that the focusing position of the low coherence optical radiation is fixed, whereas the position of the coherence gate varies during longitudinal scanning. The later limits the transverse resolution of the method and apparatus based thereon, especially for a large scanning depth. This is due to a strong diffraction divergence of sharply focused radiation and, consequently, small depth resolution. For instance, the depth resolution for a focused Gaussian beam is $d=\pi\Phi^2/4\lambda$, where $\Phi$ is the beam waist diameter, $\lambda$ is the wavelength, and $\pi=3.1416$. Accordingly, for typical parameters of $\Phi=0.005$ mm, $\lambda=1300$ nm, the depth resolution is as small as 0.015 mm (15 µm).

To ensure a high transverse resolution for a large depth of longitudinal scanning, known apparatus perform synchronous scanning of the focal waist position, i.e., of the focusing position of the optical radiation, by moving one of the lenses of the optical system, and of the position of the coherence gate by altering the relative optical lengths of the interferometer arms. This approach is referred to as optical coherence microscopy (OCM). All known embodiments of OCM perform these two scans (of the focusing position and coherence gate position) by means of two independent synchronously operating devices. The synchronization of these devices is an independent and fairly complicated engineering task, which becomes even more complicated as the speed of the image input increases.

SUMMARY OF INVENTION

The present invention is directed to a method and apparatus for imaging an object using low coherence optical radiation and to a delivering device for low coherence optical radiation, which is part of the apparatus. The invention ensures obtaining of undistorted, plane images of a flat object, as well as high transverse resolution of the method and apparatus carrying out this method, and of the delivering device for low coherence optical radiation.

According to the developed method for imaging an object, one part of a low coherence optical radiation is directed to the object through an optical system, which ensures focusing the low coherence optical radiation onto the object. This part of the low coherence optical radiation is simultaneously scanned over a transverse scanning surface in compliance with a predetermined rule, wherein the transverse scanning surface is approximately orthogonal to the direction of propagation of said optical radiation. Another part of the low coherence optical radiation is directed along a reference path. The optical radiation having returned from the object is then combined with the optical radiation, which passed along the reference optical path. The optical radiation, which is a result of the combining, is used to visualize the intensity of the optical radiation returned from the object.

Unlike the prior methods according to the invention, a constant propagation time is provided for the low coherence optical radiation propagating from a given point of the transverse scanning surface to a corresponding conjugate point of the image plane, thereby eliminating the transverse scanning related aberration of the optical path length for the low coherence optical radiation directed towards the object.

It is advisable to perform additional longitudinal scanning for given coordinates of the transverse scanning surface by varying, in compliance with a predetermined rule, the difference between the optical path lengths for the low coherence optical radiation directed towards the object and low coherence optical radiation directed along the reference path.

In a particular embodiment, the difference between the optical path lengths for the low coherence optical radiation directed towards the object and low coherence optical radiation directed along the reference path is varied by at least several tens of wavelengths of the low coherence optical radiation.

In another particular embodiment the difference between the optical path lengths is varied by altering the optical path length for the low coherence radiation propagating from the transverse scanning surface to the optical system.

In another particular embodiment the object is a biological tissue of a living body.

In a specific embodiment the object is an internal cavity of the living body.

In another specific embodiment, the low coherence optical radiation is an optical radiation in the visible or near infrared range.

The developed apparatus for imaging an object, comprises a source of low coherence optical radiation optically coupled with an interferometer and at least one photodetector, which is connected with a data processing and displaying unit. The interferometer comprises a beam splitter optically coupled with a measuring arm and a reference arm, the measuring arm being provided with a delivering device for low coherence optical radiation. The delivering device comprises an optical fiber optically coupled with an optical system, and a system for transverse scanning of the low coherence optical radiation. The optical fiber is positioned allowing for the low coherence optical radiation to pass from the proximal end of the delivering device to its distal end. The optical system provides focusing of the low coherence optical radiation onto the object and includes at least a first lens component with positive focal power. The optical fiber is incorporated into the system for transverse scanning, which is arranged capable of moving the end face of the distal part of the optical fiber over the transverse scanning surface in a direction approximately perpendicular to the own axis of the optical fiber.

Unlike the prior devices, according to the invention, the optical system of the delivering device for low coherence optical radiation is designed to have a quality of eliminating the transverse scanning related aberration of the optical length of the measuring arm. The optical system comprises at least a second lens component with positive focal power, which is positioned after the first lens component.

In one particular embodiment, the transverse scanning surface is characterized by a by a non-zero curvature.

In a specific embodiment, the optical fiber serves as a flexible cantilever and is fixedly attached to a bearing support incorporated into the delivering device for low coherence optical radiation.

In another particular embodiment, the first and second lens components of the optical system are positioned substantially confocally.

In a different particular embodiment, the first lens component of the optical system is placed at a distance substantially equal to the focal length of the first lens component from the transverse scanning surface, while the distance between the first and second lens components of the optical system is diverse from that corresponding to a substantially confocal position of the lens components by a value $\delta 1$, which is related with the focal length $F1$ of the first lens component and the radius of curvature $R$ of the transverse scanning surface by the following relation:

$$\delta 1 \cong (F1)^2/R.$$

In another particular embodiment, the first lens component of the optical system is offset by a distance $\delta 2$ from the position at which the distance from the first lens component to the transverse scanning surface is substantially equal to the focal length $F1$ of this lens component, while the distance between the first and second lens components of the optical system is diverse from the distance corresponding to the substantially confocal position of these lens components by a value $\delta 3$, which is given by the relation:

$$\delta 3 \cong (F1)^2/(R+\delta 2).$$

In another particular embodiment, the delivering device for low coherence optical radiation is designed as an optical fiber probe.

In another particular embodiment, at least one interferometer arm is additionally provided with a device for longitudinal scanning.

In a specific embodiment, the device for longitudinal scanning is placed in the measuring arm of the interferometer and is designed to provide altering the optical length of the part of the measuring arm located between the transverse scanning surface and the optical system.

In a particular embodiment when imaging a subsurface part of the object, the magnification factor $M$ of the optical system is related to the refractive index $N1$ of the object as follows: $M=1/N1$.

In another particular embodiment when imaging a profile of the object, the magnification factor $M$ of the optical system is related to the refractive index $N2$ of the medium adjoining the surface of the object as follows: $M=1/N2$.

In another embodiment, the device for longitudinal scanning is placed inside the delivering device for low coherence optical radiation.

In another particular embodiment, the end face of the optical fiber is provided with a microlens, which is rigidly attached to the optical fiber.

The developed delivering device for low coherence optical radiation, comprises an optical fiber optically coupled with an optical system and a system for transverse scanning of the low coherence optical radiation. The optical fiber is positioned allowing for low coherence optical radiation to pass from the proximal end of the delivering device to its distal end. The optical system provides focusing the low coherence optical radiation onto the object and includes at least a first lens component with positive focal power. The optical fiber is incorporated into the system for transverse scanning, which is arranged capable of moving the end face of the distal part of the optical fiber over a transverse scanning surface in a direction approximately perpendicular to the own axis of the optical fiber.

Unlike the prior delivering devices, according to the invention, the optical system is designed having a quality of eliminating the transverse scanning related aberration of the optical path length for the low coherence optical radiation passing through the delivering device. The optical system comprises at least a second lens component with positive focal power, which is positioned after the first lens component.

In a particular embodiment, the transverse scanning surface is characterized by a non-zero curvature.

In a specific embodiment, the optical fiber serves as a flexible cantilever and is fixedly attached to a bearing support incorporated into the delivering device for low coherence optical radiation.

In another particular embodiment, the first and second lens components of the optical system are positioned substantially confocally.

In a different particular embodiment, the first lens component of the optical system is placed at a distance substantially equal to the focal length of the first lens component from the transverse scanning surface, while the distance between the first and second lens components of the optical system is diverse from the distance corresponding to the substantially confocal position of the lens components by a value $\delta 1$, which is related to the focal length $F1$ of the first lens component and the radius of curvature $R$ of the transverse scanning surface by the following relation:

$$\delta 1 \cong (F1)^2/R.$$

In another particular embodiment, the first lens component of the optical system is offset by a distance $\delta 2$ from the position at which the distance from the first lens component to the transverse scanning surface is substantially equal to the focal length $F1$ of this lens component, while the distance between the first and second lens components of the optical system is diverse from the distance corresponding to the substantially confocal position of these lens components by a value $\delta 3$, which is given by the relation:

$$\delta 3 \cong (F1)^2/(R+\delta 2).$$

In another particular embodiment, the delivering device for low coherence optical radiation is designed as an optical fiber probe, whereas the optical fiber, the optical system and the system for transverse scanning of low coherence radiation are encased into an elongated body with a throughhole extending therethrough, the optical fiber extending through the throughhole.

In another particular embodiment, an output window of the delivering device for low coherence optical radiation is arranged near the image plane of the end face of the distal part of the optical fiber.

In a specific embodiment, the second lens component of the optical system serves as the output window of the delivering device for low coherence optical radiation.

In another specific embodiment, the normal line to the outer surface of the output window of the delivering device for low coherence optical radiation is oriented at an angle to the direction of incidence of the low coherence optical radiation on the outer surface, the angle exceeding the divergence angle of the low coherence optical radiation at the place of its intersection with the outer surface.

In a particular embodiment when using a one-coordinate substantially linear trajectory of transverse scanning the second lens component is offset both in a direction that is orthogonal to the direction of transverse scanning, and in a direction that is orthogonal to the direction of propagation of the low coherence optical radiation.

In another particular embodiment, the delivering device is provided additionally with a device for longitudinal scanning designed as a device for altering the optical path length for the low coherence optical radiation from the transverse scanning surface to the optical system.

In a specific embodiment for imaging a subsurface part of the object, the magnification factor M of the optical system is related to the refractive index N1 of the object as follows: M=1/N1.

In another specific embodiment for imaging a profile of the object the magnification factor M of the optical system is related to the refractive index N2 of the medium adjoining the surface of the object as follows: M=1/N2.

In another particular embodiment, the end face of the optical fiber is provided with a microlens, which is rigidly attached to the optical fiber.

In the present invention a constant propagation time is provided for the low coherence optical radiation propagating from a given point of the transverse scanning surface, i.e., from the end face of the distal part of the optical fiber, which is aligned with the transverse scanning surface, to a corresponding conjugate point of the image plane. That assures exclusion of the transverse scanning related aberration of the optical path length for the low coherence optical radiation directed towards the object. This is achieved by designing the optical system comprising at least two lens components with positive focal power, which are placed substantially confocally. Therewith, both for a flat transverse scanning surface and a transverse scanning surface with a curvature the first lens component can be positioned at a distance equal to the focal length of this lens component from the transverse scanning surface, as well as at a distance somewhat greater or smaller than its focal length. In the case when the transverse scanning surface has a curvature, additional aberration induced by this curvature is compensated by a corresponding induced aberration with an opposite sign. In addition, performing the longitudinal scanning by varying the optical path length for the low coherence optical radiation from the transverse scanning surface to the optical system and, consequently, to the object as well, ensures a corresponding shift of the focusing position of the low coherence optical radiation during longitudinal scanning. A constant propagation time for the low coherence optical radiation propagating from a given point of the transverse scanning surface, i.e., from the end face of the distal part of the optical fiber, to a corresponding conjugate point of the image plane, and the particular above mentioned way of longitudinal scanning, being jointly implemented in this invention, provide alignment of the focusing position of the low coherence optical radiation with the position of the coherence gate and, consequently, their simultaneous movement. This avoids the necessity to use additional synchronizing devices required in prior art technique. This implementation ensures a high transverse resolution of the method and apparatus carrying out this method.

Orienting the normal line to the outer surface of the output window of the optical fiber probe at an angle to the direction of incidence of the low coherence optical radiation on said outer surface, which exceeds the angle of divergence of the low coherence optical radiation in the place of its intersection with said outer surface, prevents the reflected radiation from being backscattered into the optical fiber. Particular types and shapes of the second lens component characterize the invention in its particular specific embodiments.

Thus the suggested method for imaging an object, an apparatus for carrying out this method and a delivering device for low coherence optical radiation, which is part of the apparatus, allow for obtaining a non-distorted plane image of a flat object and are characterized by a high transverse resolution.

BRIEF DESCRIPTION OF DRAWINGS

The features and advantages of the invention will be apparent from the following detail description of preferred embodiments with reference to the accompanying drawings, in which.

MODES FOR CARRYING OUT THE INVENTION

The developed method for imaging an object, an apparatus for carrying out this method, and a device for delivering low coherence optical radiation are exemplified by an optical fiber interferometer incorporated into an optical low coherence tomography device, and an optical fiber probe, although it is obvious that they can be realized by means of optical elements with lumped parameters.

The operation of the developed apparatus for imaging an object and of the device for delivering low coherence optical radiation, designed in a specific embodiment as an optical fiber probe, will be best understood from the following description of carrying out the method for imaging an object.

Figure 1:
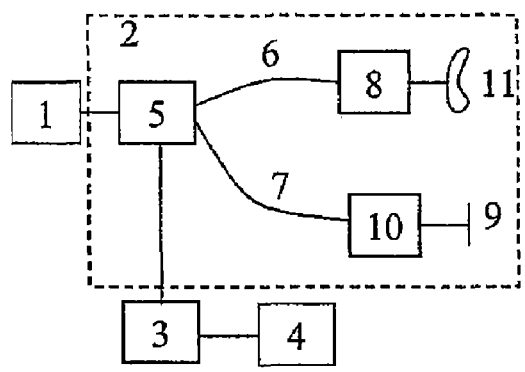
FIG. 1 is a schematic diagram of one particular embodiment of the developed apparatus for imaging an object suitable for implementing the developed method for imaging an object.
Figure 2:
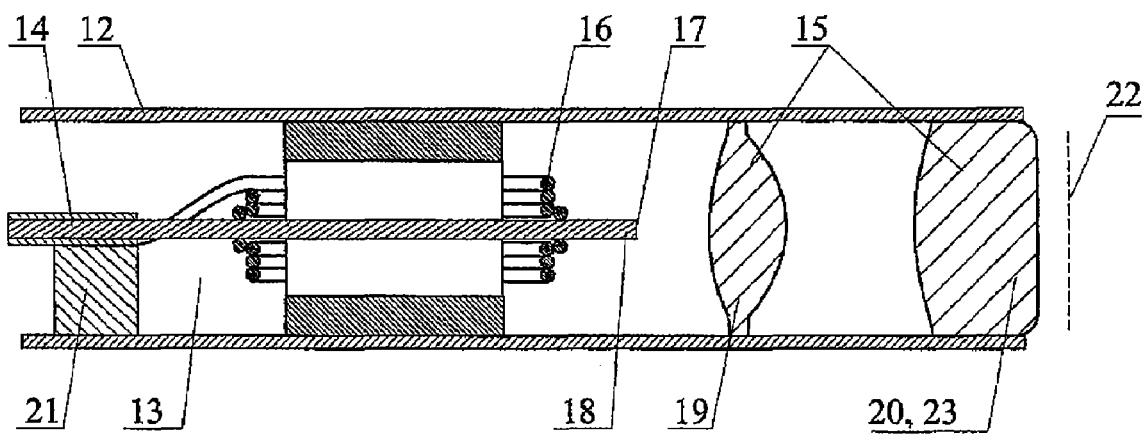
FIG. 2 is a cross-sectional view of one particular embodiment of the optical fiber probe.

The method for imaging an object is carried out the following way with the aid of the apparatus of the invention, as depicted in FIG. 1, and with the aid of the optical fiber probe shown in FIG. 2, whose particular embodiments of the optical system are presented in FIG. 3, FIG. 4, FIG. 5, FIG. 6 and FIG. 7.

An optical fiber probe 8 (FIG. 2) with an elongated body 12 is positioned so as to ensure focusing of the low coherence optical radiation onto an object 11. The optical fiber probe 8 is made miniature (see FIG. 2) and may be placed at the distal end of the instrumental channel of an endoscope (not shown in the drawing). In a particular embodiment designed for endoscopic studies, the length of the body 12 is no more than 27 mm, whereas its diameter is no more than 2.7 mm. For better serviceability the distal part of the optical fiber probe 8 may have changeable tips.

The body 12 of the optical fiber probe 8, which may be made of stainless steel, has a throughhole 13 extending therethrough. An optical fiber 14, an optical system 15 and a transverse scanning system 16 connected with a source of control current (not shown in the drawing) are placed in the throughhole 13 in a longitudinal direction. The optical fiber 14 preferably should be single-mode polarization-maintaining fiber; for instance, an optical fiber of PANDA-type may be used. An end face 17 of a distal part 18 of the optical fiber 14 is optically coupled with the optical system 15.

The optical system 15, which comprises at least two lens components with positive focal power, ensures focusing of the low coherence optical radiation onto the object 11. In a particular embodiment referred to in FIG. 2, the optical system 15 includes a first lens component 19 and a second lens component 20, which are positioned in series along the optical axis. In one embodiment of the optical fiber probe 8 shown in FIG. 2, an output window 23 of the optical fiber probe 8 is placed near to an image plane 22 of the end face 17 of the distal part 18 of the optical fiber 14. In this embodiment the lens component 20 of the optical system 15 serves as an output window 23 of the optical fiber probe 8.

Figure 3:
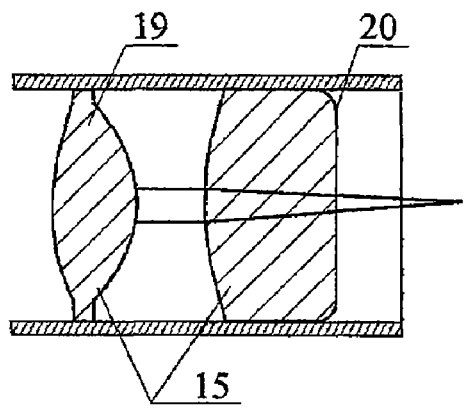
FIG. 3 is a cross-sectional view of one particular embodiment of the optical system of the optical fiber probe.

The optical system 15 of the optical fiber probe 8 may comprise no output window; this embodiment of the optical system 15 is depicted in FIG. 3.

Figure 4:
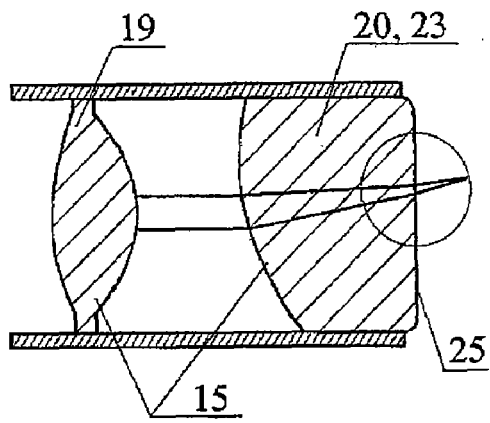
FIG. 4 is a cross-sectional view of another particular embodiment of the optical system of the optical fiber probe.
Figure 4:
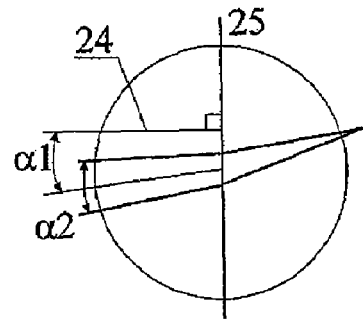

The optical system 15 is preferably designed according to FIG. 4. Here a normal line 24 to the outer surface 25 of the output window 23 of the optical fiber probe 8 is oriented at an angle $\alpha_1$ to the direction of incidence of the low coherence optical radiation at the place of its intersection with the outer surface 25. In this embodiment, the second lens component 20 is offset both in the orthogonal direction relative to the direction of transverse scanning and in the orthogonal direction relative to the direction of propagation of the low coherence optical radiation. In this particular embodiment the second lens component 20 is designed as a spherical lens, and the offsetting is realized by shifting the center of curvature of the lens component.

Figure 5:
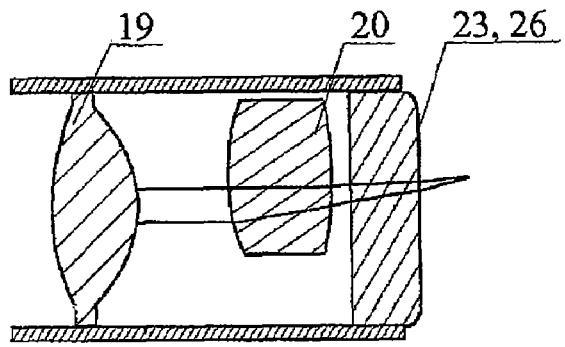
FIG. 5 is a cross-sectional view of a different particular embodiment of the optical system of the optical fiber probe.

FIG. 5 illustrates another way of offsetting the second lens component 20. Here the abovementioned provision is fulfilled too, concerning the orientation of the normal line 24 to the direction of incidence of the low coherence optical radiation onto the outer surface 25 of the output window 23. In this embodiment the output window 23 is made as a plane-parallel plate 26.

Figure 6:
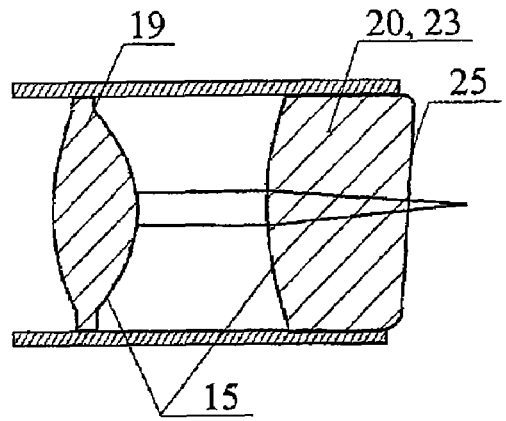
FIG. 6 is a cross-sectional view of another particular embodiment of the optical system of the optical fiber probe.
Figure 7:
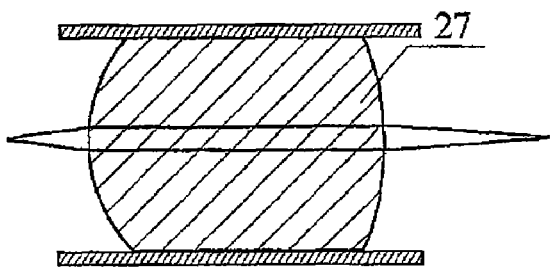
FIG. 7 is a cross-sectional view of another particular embodiment of the optical system of the optical fiber probe.
Figure 8:
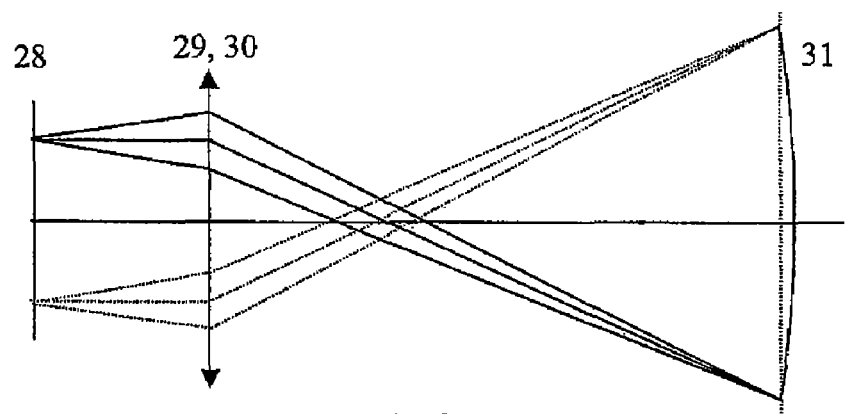
FIG. 8 illustrates construction of an image with the aid of prior technique.
Figure 9:
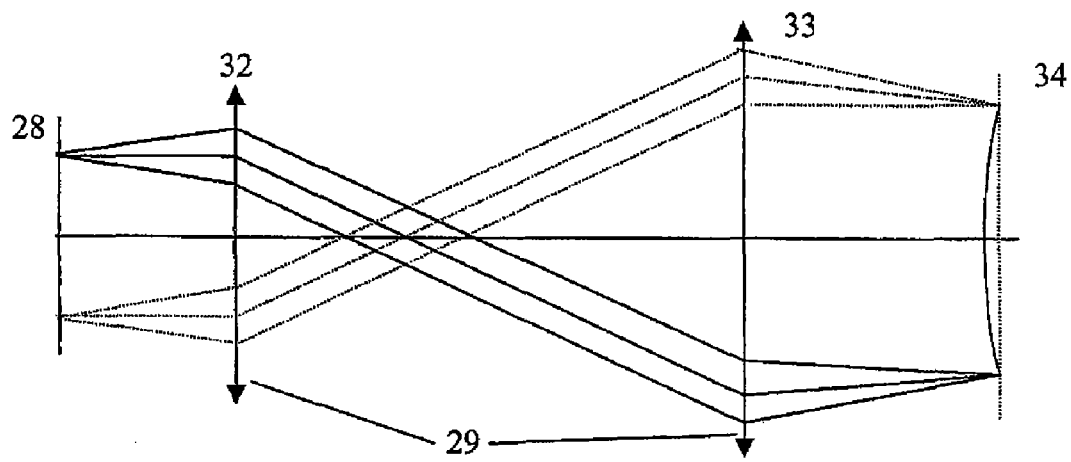
FIG. 9 illustrates the construction of an image by using another prior technique.
Figure 10:
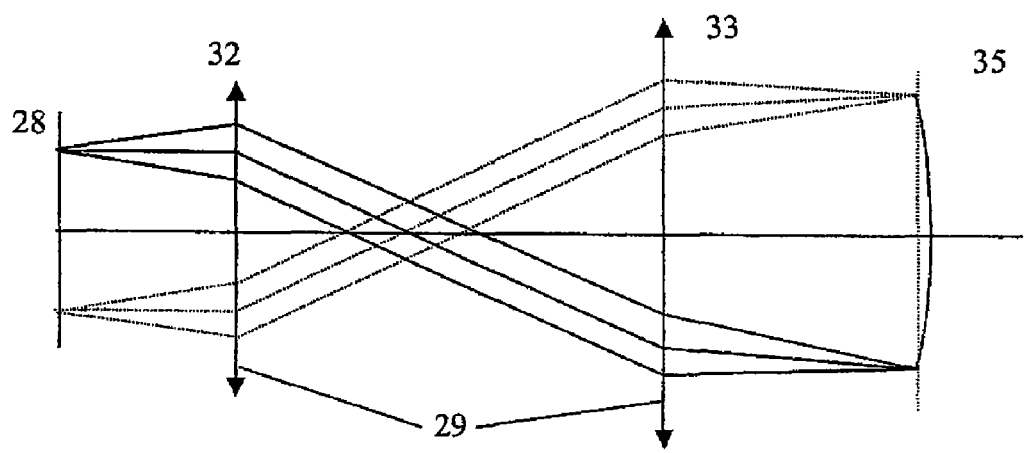
FIG. 10 illustrates the construction of an image by using another prior technique.

In one embodiment of the optical system 15 shown in FIG. 6, the second lens component 20 serves as the output window 23. The outer surface 25 of the lens component 20 is beveled in order to meet the above orienting provision for the normal line 24 to the direction of incidence of the low coherence optical radiation on the outer surface 25 of the output window 23.

The optical system 15 is preferably made as a composite lens 27 (FIG. 7) incorporating the first lens component 19 and second lens component 20.

Both the first lens component 19 and second lens component 20 are preferably made as a gradient lens. The optical system 15 of the optical fiber probe 8 may be arranged as a gradient lens too, incorporating the first lens component 19 and second lens component 20 (not shown in the drawing). Both the first lens component 19 and second lens component 20 in different particular embodiments of the optical system 15 may be made as a composite lens. These embodiments are not shown in the drawings.

The first lens component 19 and second lens component 20 may comprise various optical elements needed, for instance, for correction of aberrations of different origin. To improve the quality of obtained images it is advisable to make the first lens component 19 and second lens component 20 aspherical.

In all embodiments of the optical fiber probe 8 the distance between the second lens component 20 and the image plane 22 is determined by the provision that the low coherence optical radiation directed towards the object 11 must be focused onto the image plane 22.

In a particular embodiment when the optical fiber probe 8 is an endoscopic probe, the optical fiber probe 8 is positioned in a way that the outer surface 25 of the output window 23 is brought into contact with the object 11. The object 11 in a particular embodiment is a biological tissue of a living body, in particular, an internal cavity of the living body.

Low coherence optical radiation, in a particular embodiment in the visible and near IR range, is formed using a source 1, which can be arranged, for example, as a laser or a superluminescent diode. The low coherence optical radiation is directed simultaneously towards the object 11 and along the reference path. For this, the low coherence optical radiation is split into two portions by means of a beam splitter 5, which is part of an optical fiber interferometer 2 optically coupled with the source 1. The interferometer 2 can be an optical interferometer of any type, for instance, a Michelson interferometer, a Mach-Zender interferometer, or combinations of these interferometers known, for example, from International patent application No. WO 00/16034. In the embodiment referred to in FIG. 1, the optical fiber interferometer 2 is arranged as a Michelson interferometer. A portion of the optical radiation from the output of the beam-splitter 5 is directed towards the object 11 with the aid of an optical fiber measuring arm 6 optically coupled with the beam-splitter 5, and with the aid of the delivering device for low coherence optical radiation designed in this particular embodiment as an optical fiber probe 8 incorporated into the measuring arm 6. This portion of optical radiation passes through a section of the optical fiber 14 from a proximal end of the optical fiber 14 to its distal end 18 (FIG. 2).

A part of the measuring arm 6 of the optical fiber interferometer 2 may be made flexible and introduced into the instrumental channel of an endoscope (not shown in the drawing). A part of the measuring arm 6 of the interferometer 2, including the part being introduced into the instrumental channel of an endoscope, may be made changeable and connected by a detachable connection with the main part of the measuring arm 6. The changeable part of the measuring arm 6 of interferometer 2 may be made disposable.

Figure 16:
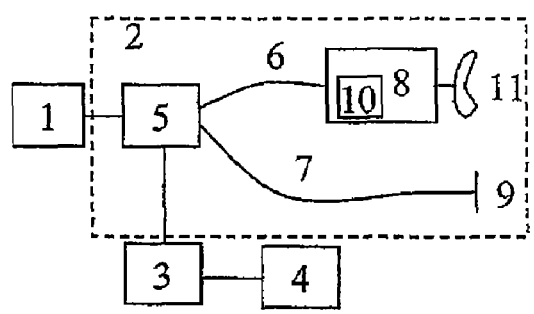
FIG. 16 shows a schematic diagram of another embodiment of the developed apparatus for imaging an object suitable for implementing the developed method.

While delivering the portion of optical radiation to the object 11, transverse scanning of this portion of optical radiation is performed by moving the distal part 18 of the optical fiber 14 in a direction approximately perpendicular to the axis of the optical fiber 14 with the aid of a transverse scanning system 16 (FIG. 16). The transverse scanning system 16 is designed capable of moving the distal part 18 of the optical fiber 14 in a direction approximately perpendicular to the axis of the optical fiber 14. In a particular embodiment shown in FIG. 2 the optical fiber 14 serves as a flexible cantilever and is fixedly attached to a bearing support 21 incorporated into the optical fiber probe 8. The transverse scanning system 16 may be made, for example, similar to the device known from RU Pat. No. 2,148,378 which is incorporated herein by reference. During transverse scanning, a constant propagation time is provided for the low coherence optical radiation propagating from a given point of the transverse scanning surface to a corresponding conjugate point of the image plane. Thereby the transverse scanning related aberration of the optical path length directed towards the object 11 is eliminated, the later being achieved due to an appropriate geometry of the optical system 15.

Figure 11:
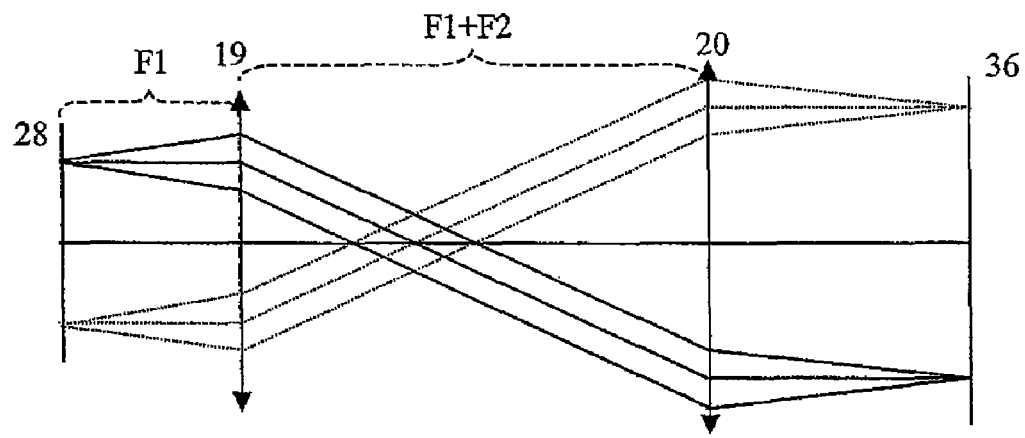
FIG. 11 illustrates the procedure of eliminating the aberration of the optical path length for the low coherence optical radiation directed to an object by means of one modification of the invention for a flat transverse scanning surface.
Figure 12:
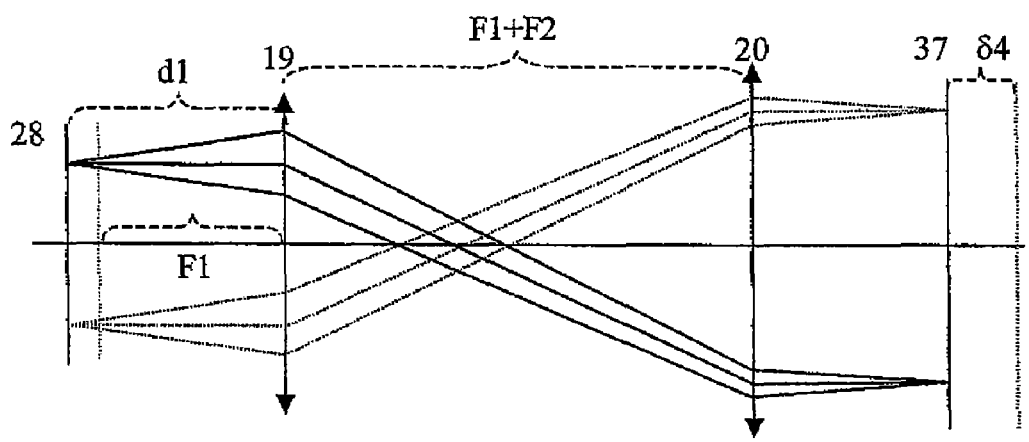
FIG. 12 illustrates the procedure of eliminating the aberration of the optical path length for the low coherence optical radiation directed towards the object by means of another modification of the invention for a flat transverse scanning surface.
Figure 13:
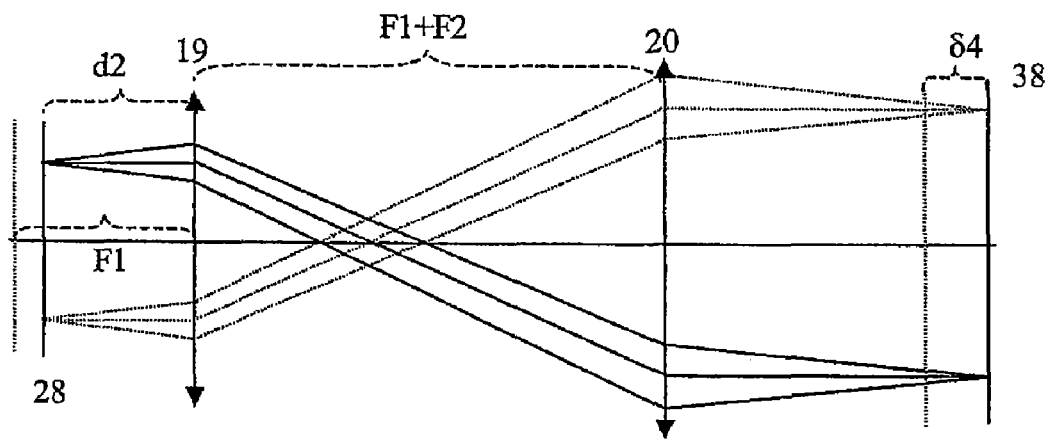
FIG. 13 illustrates the procedure of eliminating the aberration of the optical path length for the low coherence optical radiation directed towards the object by means of another modification of the invention for a flat transverse scanning surface.

In particular, when the transverse scanning surface 28 is flat, the first lens component 19 and second lens component 20 of the optical system 15 are placed substantially confocally (FIG. 11, FIG. 12 and FIG. 13). FIG. 11 illustrates a case when the first lens component 19 is placed at a distance that is substantially equal to the focal length F1 of this component from the surface 28; FIG. 12 illustrates a case when the first lens component 19 is placed at a distance d1 that is slightly greater than the focal length F1 from the scanning surface 28; and in FIG. 13 the first lens component 19 is placed at a distance d2 that is slightly less than the focal length F1 from the surface 28. When a scanning surface 39 has a curvature (FIG. 14), the first lens component 19 of optical system 15 is placed at a distance that is substantially equal to the focal length F1 of this lens component from the transverse scanning surface 39. In this case, the distance between the first lens component 19 and second lens component 20 of the optical system 15 is diverse from the distance corresponding to the substantially confocal position of lens components 19 and 20 of the optical system 15 by a value $\delta1$ related to the focal length F1 of the first lens component 19 and the radius of curvature R of the transverse scanning surface 39 by the following relation:

$$\delta1 \cong (F1)^2/R.$$

In another modification, when the scanning surface 39 has a curvature (FIG. 15), the first lens component 19 of the optical system 15 is offset by a distance $\delta2$ from the position at which the distance from the first lens component 19 to the transverse scanning surface 39 is substantially equal to the focal length F1 of the first lens component 19, while the distance between the first and the second lens components 19, 20 of the optical system 15 is diverse from the distance corresponding to the substantially confocal position of lens components 19 and 20 by a value $\delta3$, which is given by the following relation:

$$\delta3 \cong (F1)^2/(R+\delta2).$$

Another portion of the low coherence optical radiation is directed along the reference path with the aid of a reference arm 7, optically coupled with the beam splitter 5 of the optical fiber interferometer 2. In this embodiment, a reference mirror 9 is installed at the end of the reference arm 7. The reference arm 7 comprises a device 10 that is designed to vary the difference in the optical lengths of the arms of the interferometer 2 to provide longitudinal scanning in the object 11. The device 10 is connected with a source of control voltage (not shown in the drawing). Referring to FIG. 1, the reference mirror 9 is stationary, whereas the device 10 is made as an optical fiber piezoelectric transducer known from RU Pat. No. 2,100,787. In this embodiment, the device 10 comprises at least one piezoelectric element, which is arranged capable of forming an electric field in it and exhibits a high perpendicular inverse piezoeffect, electrodes, which are rigidly connected with the piezoelectric element, and an optical fiber, which is rigidly connected with the electrodes. A dimension of the piezoelectric element in a direction substantially orthogonal with the electric field vector is essentially larger than a dimension of the piezoelectric element in a direction substantially aligned with the electric field vector. The length of the optical fiber exceeds substantially the diameter of the piezoelectric element.

The device 10 may be made analogous with scanners described in U.S. Pat. No. 5,321,501. In this case, the reference mirror 9 is made movable at a constant speed, and the device 10, being connected with the reference mirror 9, may be made as mechanisms of different types described in the above patent, providing necessary moving of the reference mirror 9. The device 10 may also be designed according to the paper by K. F. Kwong, D. Yankelevich et al, "400-Hz mechanical scanning optical delay line", Optics Letters, Vol. 18, No. 7, Apr. 1, 1993, as a disperse grating delay line, which is incorporated by reference herein.

Figure 14:
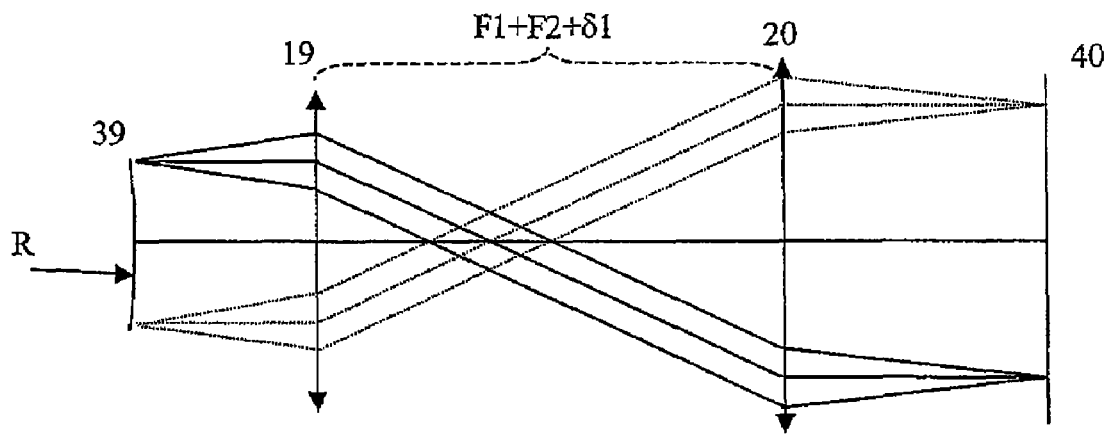
FIG. 14 illustrates the procedure of eliminating the aberration of the optical path length for the low coherence optical radiation directed towards the object by means of another modification of the invention for a transverse scanning surface having a curvature.
Figure 15:
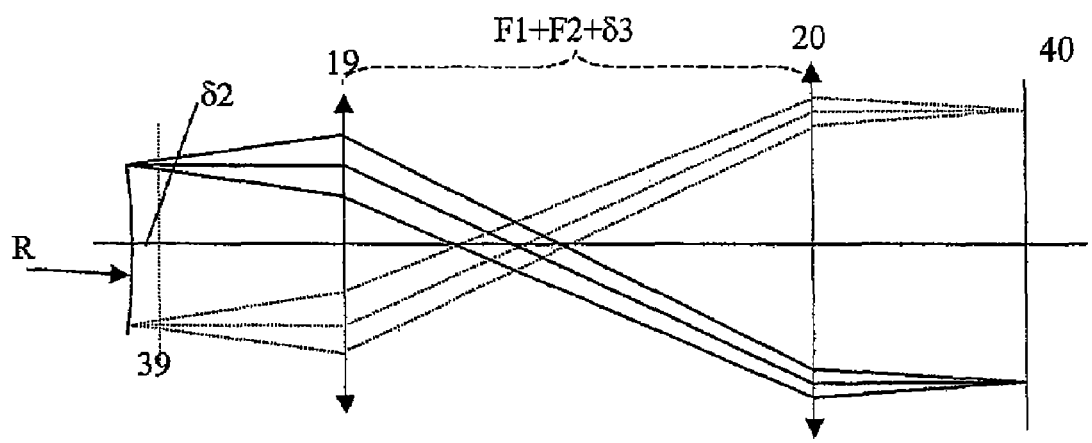
FIG. 15 illustrates the procedure of eliminating the aberration of the optical path length for the low coherence optical radiation directed towards the object by means of another modification of the invention for a transverse scanning surface having a curvature.

With the aid of the device 10 the difference between optical lengths of the arms 6 and 7 of the interferometer 2 is varied, in compliance with a predetermined rule, at a constant velocity V for given coordinates in the transverse scanning surface 28 (FIG. 11, FIG. 12, FIG. 13) or for given coordinates in the transverse scanning surface 39 (FIG. 14, FIG. 15). Thereby the difference in the optical path lengths for the low coherence optical radiation directed towards the object 11 and along the reference path is changed too.

With the aid of the beam splitter 5 the optical radiation that returned from the object 11 is then combined with the optical radiation, which passed along the reference path, in the particular embodiment, with the optical radiation reflected from the reference mirror 9. The mentioned change in the difference between the optical lengths of the arm 6 and the arm 7, provided by the device 10, leads to interference modulation of the intensity of the combined optical radiation at the output of the beam splitter 5 at a Doppler frequency f=2V/λ, where λ is the operating wavelength of the source 1. The rule of interference modulation corresponds to the change in the intensity of the optical radiation returned from the object 11. Then an image of the object 11 is obtained by using the result of said combining to visualize the intensity of the optical radiation that returned from the object 11. The latter is done as follows.

A photodetector 3, which may be a photodiode connected with the interferometer 2, provides for conversion of the combined optical radiation from the output of the beam splitter 5 into an electrical signal. In this embodiment, the device for imaging an object comprises a single photodetector, but it is evident that any other known detection technique may be used. The electrical signal arrives at a processing and displaying unit 4 connected with the output of the photodetector 3. The processing and displaying unit 4 is used to form an image of the object 11 by visualizing the intensity of the optical radiation that returned from the object 11. Unit 4 may be made, for example, similar to the data processing and displaying unit discussed in the paper by V. M. Gelikonov et al., "Coherence optical tomography of microinhomogeneities in biological tissues" JETP Lett., v. 61, No 2, pp. 149-153, which is incorporated by reference herein. This data processing and displaying unit comprises a band-pass filter, a log amplifier, an amplitude detector, an analog-to-digital converter, and a computer, all these elements being connected in series.

The band-pass filter of unit 4 sorts the signal at a Doppler frequency, thereby improving the signal-to-noise ratio. Once the signal is amplified, it arrives at an amplitude detector that sorts a signal proportional to the waveform envelope of this signal. The signal sorted by the amplitude detector of unit 4 is proportional to the signal of interference modulation of the intensity of the combined optical radiation. Analog-to-digital converter of unit 4 converts the signal from the output of the amplitude detector into a digital format. Computer of unit 4 provides for acquisition of images by displaying on a video monitor the intensity of the digital signal (the displaying may be performed as described, for instance, in the book by H. E. Burdick "Digital imaging: Theory and Applications", 304 pp., Me Graw Hill, 1997, which is incorporated by reference herein). Since the digital signal corresponds to the change in intensity of optical radiation that returned from the object 11, the image displayed on the monitor corresponds to an image of the object 11.

FIG. 11, FIG. 12 and FIG. 13 illustrate the construction of an image by means of the invention in a case of a flat transverse scanning surface 28. Lines 36, 37, and 38 in the image plane in FIG. 11, FIG. 12 and FIG. 13, respectively, correspond to a point locus, to which the propagation time and hence the optical path length has the same value for the low coherence optical radiation passing to the object 11 from corresponding conjugate points disposed at various off axis positions in the flat transverse scanning surface 28. It can be seen from the figures that when the first lens component 19 and second lens component 20 of the optical system 15 are placed substantially confocally, the lines 36, 37, and 38 have no curvature. The later stays true when the first lens component 19 is placed at a distance substantially equal to the focal length F1 of this lens component from the surface 28 (FIG. 11), as well as at a distance d1 greater than the focal length F1 (FIG. 12), or at a distance d2 smaller than the focal length F1 (FIG. 13) from the surface 28. Depending on the position of the first lens component 19, lines 37 and 38 are shifted to this or that direction relative the position of line 36 by some value δ4.

FIGS. 14, 15 illustrate the construction of an image by means of the invention in a case when the transverse scanning surface 39 has a curvature. A line 40 in the image plane corresponds to a point locus, to which the propagation time and hence the optical path length has the same value for the low coherence optical radiation passing to the object 11 from corresponding conjugate points disposed at various off axis positions in the transverse scanning surface 39. It is seen from these figures that the line 40 has no curvature. Provided the aforementioned conditions of mutual positioning of the first lens component 19 and the second lens component 20 are fulfilled, the line 40 has no curvature when the first lens component 19 is placed at a distance substantially equal to the focal length F1 of this lens component from the surface 39, as well as at a greater or smaller distance than its focal length F1.

Figure 17:
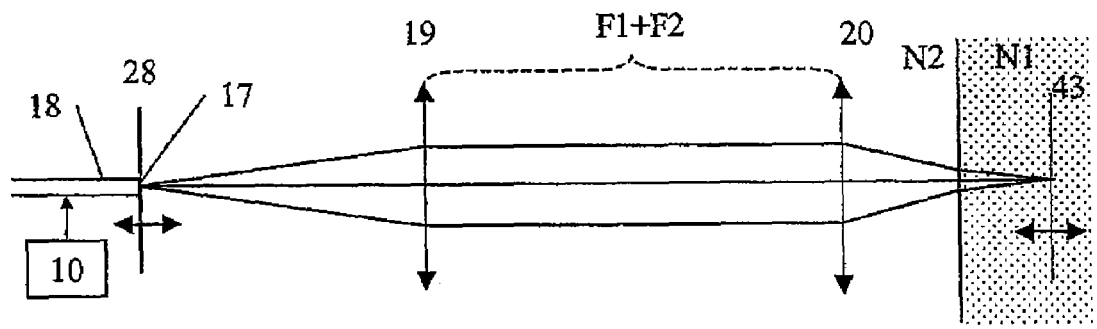
FIG. 17 illustrates one embodiment of the optical fiber probe incorporating a device for longitudinal scanning, which is designed as a device for varying the optical path length for the low coherence optical radiation propagating from the end face of the optical fiber to the optical system.
Figure 18:
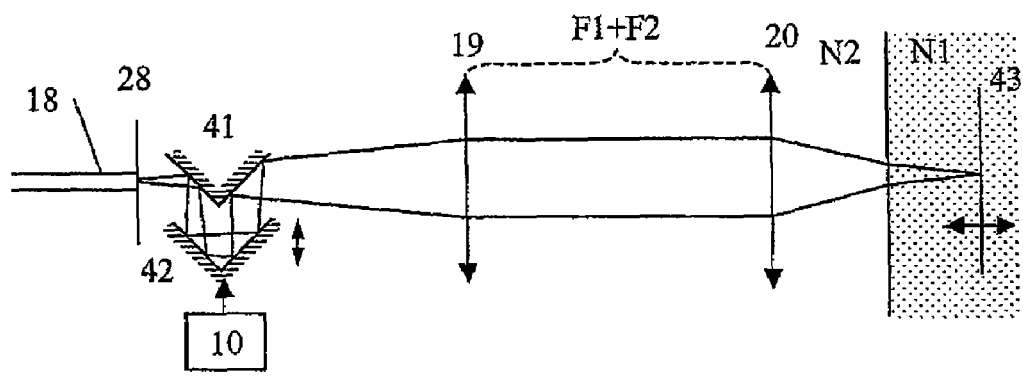
FIG. 18 illustrates another embodiment of the optical fiber probe incorporating a device for longitudinal scanning, which is arranged as a device for varying the optical path length for the low coherence optical radiation propagating from the end face of the optical fiber to the optical system.

The method for obtaining an image of an object with the aid of the apparatus, whose schematic diagram is presented in FIG. 16, is performed similarly as with the aid of the apparatus referred to in FIG. 1. The only distinction is that the difference in the optical paths lengths for the low coherence optical radiation directed towards the object 11 and directed along the reference path is varied by changing the optical path length for the low coherence optical radiation propagating from the transverse scanning surface 28, i.e., from end the face 17 of the distal part 18 of the optical fiber 14, to the optical system 15, i.e., to the object 11. To achieve this, in the apparatus referred to in FIG. 16, the device 10 for transverse scanning of the object 11 is placed within the optical fiber probe 8 and ensures changing of the optical path length for the low coherence optical radiation propagating from the transverse scanning surface 28 to the optical system 15. The optical fiber probe 8 may be made, for example, according to FIG. 17, where the device 10 is connected with the distal part 18 of the optical fiber 14. Another embodiment of the optical fiber probe 8 is shown in FIG. 18, where the optical fiber probe 8 is additionally provided with a mirror 41 and a mirror 42, while the device 10 is connected with the mirror 42. In the embodiment depicted in FIG. 17, the change in the difference of the optical path lengths is performed by appropriate moving of the distal part 18 of the optical fiber 14 with the aid of the scanning device 10, whereas in the embodiment indicated in FIG. 18—by appropriate moving of the mirror 42 with the aid of the scanning device 10. FIG. 17 and FIG. 18 show a line 43 in the image plane, which corresponds to a point locus, to which the propagation time and hence the optical path length has the same value for the low coherence optical radiation passing to the object 11 from corresponding conjugate points disposed at various off axis positions in the transverse scanning surface 28. One can see from the figure that the line 43 has no curvature. The spatial position of the line 43, i.e., the position of focusing of the optical radiation, coincides with the spatial position of the coherence gate, and this coinciding of the spatial positions is maintained during longitudinal scanning in the object 11.

In embodiments shown in FIG. 17 and FIG. 18, when imaging a subsurface part of the object 11, the magnification factor M of the optical system 15 is related to the refractive index $N_1$ of the object 11 as follows: M=1/N1, whereas when imaging a profile of the object 11 the magnification factor M of the optical system 15 is related to the refractive index N2 of the medium adjoining the surface of the object 11 as follows: M=1/N2.

In embodiments referred to in FIG. 17 and FIG. 18, the end face 17 of the distal part 18 of the optical fiber 14 may be provided with a micro lens, which is rigidly attached to the optical fiber 14 (not shown in the drawing).

Figure 19:
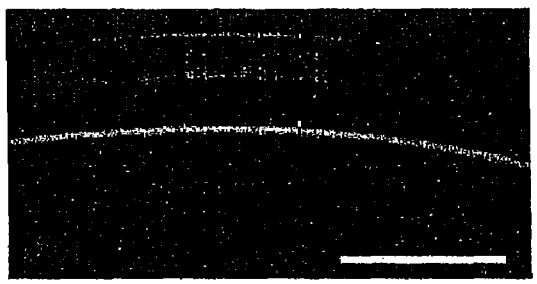
FIG. 19 is an image obtained with the aid of a prior art technique.
Figure 20:
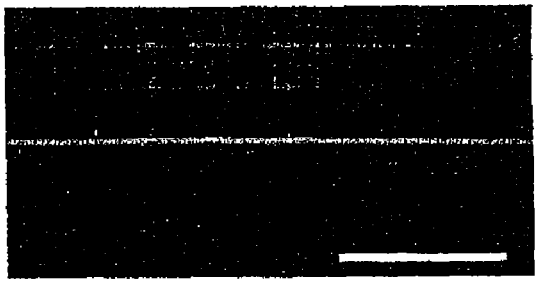
FIG. 20 is an image obtained with the aid of the invention.

FIG. 20 shows a non-distorted image obtained by means of the invention, in which the aberration of the optical path length for the low coherence optical radiation directed towards the object is eliminated, in contrast to an image obtained by means of prior art technique (FIG. 19).

The invention is suitably used in devices for studying the internal structure of objects by optical means, namely, in low coherence reflectometers and optical coherence tomography devices, which are applied, in particular, for medical diagnostics of individual organs and systems of human body in vivo and in vitro, as well as for industrial diagnostics, such as control of technological processes. It should be noted that the invention may be implemented with the aid of standard facilities.

The invention extends to computer programs in the form of source code, object code, code intermediate sources and object code (such as in a partially compiled form), or in any other form suitable for use in the implementation of the invention. Computer programs are suitably standalone applications, software components, scripts or plug-ins to other applications. Computer programs embedding the invention are advantageously embodied on a carrier, being any entity or device capable of carrying the computer program: for example, a storage medium such as ROM or RAM, optical recording media such as CD-ROM or magnetic recording media such as floppy discs. The carrier is any transmissible carrier such as an electrical or optical signal conveyed by electrical or optical cable, or by radio or other means. Computer programs are suitably downloaded across the Internet from a server. Computer programs are also capable of being embedded in an integrated circuit. Any and all such embodiments containing code that will cause a computer to perform substantially the invention principles as described, will fall within the scope of the invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for imaging an associated object, comprising the steps of:
    directing one part of a low coherence optical radiation towards an associated object through an optical system, which ensures focusing the low coherence optical radiation onto the object;
    scanning the low coherence optical radiation being directed towards an associated object over a transverse scanning surface, that is approximately orthogonal to the direction of propagation of said optical radiation;
    providing a first lens component with positive focal power after the transverse scanning surface and providing a second lens component with positive focal power after the first lens component, where the first lens component and the second lens component are positioned to provide a constant propagation time for the low coherence optical radiation propagating from a given point of the transverse scanning surface to a corresponding conjugate point of an image plane, thereby eliminating a transverse scanning related aberration of an optical path length for the low coherence optical radiation directed towards an associated object;
    directing another part of the low coherence optical radiation along a reference optical path, and
    combining an optical radiation having returned from an associated object with an optical radiation that passed through the reference optical path;
    visualizing an intensity of the optical radiation having returned from an associated object using for that an optical radiation that is a result of the combining.

2. A method as claimed in claim 1, further comprising the step of longitudinal scanning by varying a difference between the optical path lengths for the low coherence optical radiation directed towards the object and low coherence optical radiation directed along the reference optical path, said longitudinal scanning being performed for given coordinates in the transverse scanning surface in compliance with a predetermined rule.

3. A method as claimed in claim 2, wherein the difference between the optical path lengths for the low coherence optical radiation directed towards the object and low coherence optical radiation directed along the reference path is varied by at least several tens of wavelengths of the low coherence optical radiation.

4. A method as claimed in claim 2, wherein the difference between the optical path lengths is varied by altering the optical path length for the low coherence radiation propagating from the transverse scanning surface to the optical system.

5. A method as claimed in claim 1, wherein the object is a biological tissue of a living body.

6. A method as claimed in claim 5, wherein the object is an internal cavity of a living body.

7. A method as claimed in claim 1, wherein the low coherence optical radiation is an optical radiation in the visible or near infrared range.

8. An apparatus for imaging an associated object comprising:
    a source of low coherence optical radiation;
    an interferometer optically coupled to the source, the interferometer including a beam splitter optically coupled with a measuring arm and a reference arm;
    at least one photodetector connected with a data processing and displaying unit; the measuring arm being provided with a delivering device for low coherence optical radiation;
    the delivering device comprising an optical fiber optically coupled with an optical system, and a transverse scanning system for the low coherence optical radiation, the optical fiber being positioned to allow for the low coherence optical radiation to pass from the proximal end of the delivering device to its distal end, wherein the optical fiber is incorporated into the transverse scanning system, which is configured to move the end face of the distal part of the optical fiber over the transverse scanning surface in a direction approximately perpendicular to an axis of the optical fiber;
    wherein the optical system of the delivering device is configured to provide focusing of the low coherence optical radiation onto the associated object, said optical system including at least a first lens component with positive focal power and at least a second lens component with positive focal power, which is positioned after the first lens component, wherein the first lens component and the second lens component are positioned to provide constant propagation time for low coherence optical radiation propagating from a given point of the transverse scanning surface to a corresponding conjugate point of an image plane, thereby eliminating the transverse scanning related aberration of the optical length of the measuring arm.

9. An apparatus as claimed in claim 8, wherein the transverse scanning surface has a non-zero curvature.

10. An apparatus as claimed in claim 9, wherein the optical fiber serves as a flexible cantilever and is fixedly attached to a bearing support incorporated into the delivering device for low coherence optical radiation.

11. An apparatus as claimed in claim 8, wherein the first and second lens components of the optical system are positioned substantially confocally.

12. An apparatus as claimed in claim 9, wherein the first lens component of the optical system is placed at a distance substantially equal to the focal length of the first lens component from the transverse scanning surface, while the distance between the first and second lens components of the optical system is diverse from that corresponding to a substantially confocal position of the lens components by a value $\delta 1$, which is related with the focal length F1 of the first lens component and the radius of curvature R of the transverse scanning surface by the following relation:

$$\delta 1 \approx (F1)^2/R.$$

13. An apparatus as claimed in claim 9, wherein the first lens component of the optical system is offset by a distance $\delta 2$ from the position at which the distance from the first lens component to the transverse scanning surface is substantially equal to the focal length Fl of this lens component, while the distance between the first and second lens components of the optical system is diverse from the distance corresponding to the substantially confocal position of the lens components by a value $\delta 3$, which is given by the relation:

$$\delta 3 \approx (F1)^2/(R+\delta 2).$$

14. An apparatus as claimed in claim 8, wherein the delivering device for low coherence optical radiation is an optical fiber probe.

15. An apparatus as claimed in claim 8, wherein at least one interferometer arm is additionally provided with a device for longitudinal scanning.

16. An apparatus as claimed in claim 15, wherein the device for longitudinal scanning is placed in the measuring arm of the interferometer and is configured to provide altering the optical length of the part of the measuring arm located between the transverse scanning surface and the optical system.

17. An apparatus as claimed in claim 16, wherein the optical system includes a magnification factor M that is related to the refractive index N1 of a subsurface part of the object to be imaged, where M=1/N1.

18. An apparatus as claimed in claim 16, wherein the optical system includes a magnification factor M that is related to the refractive index N2 of the medium adjoining the surface of the object to be imaged, where M=1/N2.

19. An apparatus as claimed in claim 16, wherein the device for longitudinal scanning is placed within the delivering device for low coherence optical radiation.

20. An apparatus as claimed in claim 16, wherein the end face of the optical fiber is provided with a microlens, which is rigidly attached to the optical fiber.

21. A delivering device for low coherence optical radiation, comprising:
  an optical fiber optically coupled with an optical system, and a transverse scanning system for the low coherence optical radiation;
  the optical fiber being incorporated into the transverse scanning system and positioned to allow for low coherence optical radiation to pass from the proximal end of the delivering device to its distal end;
  the transverse scanning system being configured to move an end face of the distal end of the optical fiber over a transverse scanning surface in a direction approximately perpendicular to an axis of the optical fiber,
  wherein the optical system includes at least a first lens component with positive focal power and at least a second lens component with positive focal power, which is positioned after the first lens component, said optical system providing focusing the low coherence optical radiation onto an object, wherein the first lens component and the second lens component are positioned to provide constant propagation time for low coherence optical radiation propagating from a given point of the transverse scanning surface to a corresponding conjugate point of an image plane, thereby eliminating the transverse scanning related aberration of the optical length for the low coherence optical radiation passing through the delivering device.

22. A delivering device as claimed in claim 21, wherein the transverse scanning surface has a non-zero curvature.

23. A delivering device as claimed in claim 22, wherein the optical fiber serves as a flexible cantilever and is fixedly attached to a bearing support incorporated into the delivering device for low coherence optical radiation.

24. A delivering device as claimed in claim 21, wherein the first and second lens components of the optical system are positioned substantially confocally.

25. A delivering device as claimed in claim 22, wherein the first lens component of the optical system is placed at a distance substantially equal to the focal length of the first lens component from the transverse scanning surface, while the distance between the first and second lens components of the optical system is diverse from the distance corresponding to the substantially confocal position of the lens components by a value $\delta 1$, which is related to the focal length F1 of the first lens component and the radius of curvature R of the transverse scanning surface by the following relation:

$$\delta 1 \approx (F1)^2/R.$$

26. A delivering device as claimed in claim 22, wherein the first lens component of the optical system is offset by a distance $\delta 2$ from the position at which the distance from the first lens component to the transverse scanning surface is substantially equal to the focal length F1 of this lens component, while the distance between the first and second lens components of the optical system is diverse from the distance corresponding to the substantially confocal position of the lens components by a value $\delta 3$, which is given by the relation:

$$\delta 3 \approx (F1)^2/(R+\delta 2).$$

27. A delivering device as claimed in claim 21, wherein the delivering device for low coherence optical radiation is designed as an optical fiber probe, whereas the optical fiber, the optical system and the system for transverse scanning of low coherence radiation are encased into an elongated body with a throughhole extending therethrough, the optical fiber extending through the throughhole.

28. A delivering device as claimed in claim 21, wherein an output window of the delivering device for low coherence optical radiation is arranged near the image plane of the end face of the distal part of the optical fiber.

29. A delivering device as claimed in claim 28, wherein the second lens component of the optical system serves as the output window of the delivering device for low coherence optical radiation.

30. A delivering device as claimed in claim 28, wherein a normal line to an outer surface of an output window of the delivering device is oriented at an angle to the direction of incidence of the low coherence optical radiation on the outer surface, the angle exceeding a divergence angle of the low coherence optical radiation at a place of its intersection with the outer surface.

31. A delivering device as claimed in claim 30, wherein when using a one-coordinate substantially linear trajectory of transverse scanning the second lens component is offset both in a direction that is orthogonal to the direction of transverse scanning, and in a direction that is orthogonal to the direction of propagation of the low coherence optical radiation.

32. A delivering device as claimed in claim 21, wherein the delivering device is provided additionally with a device for longitudinal scanning designed as a device for altering the optical path length for the low coherence optical radiation propagating from the transverse scanning surface to the optical system.

33. A delivering device as claimed in claim 32, wherein the optical system includes a magnification factor M that is related to the refractive index N1 of a subsurface part of the object to be imaged, where M=1/N1.

34. A delivering device as claimed in claim 32, wherein the optical system includes a magnification factor M that is related to the refractive index N2 of the medium adjoining the surface of the object to be imaged, where M=1/N2.

35. A delivering device as claimed in claim 21, wherein the end face of the optical fiber is provided with a microlens, which is rigidly attached to the optical fiber.

* * * * *